United States Patent [19]

Bird

[11] Patent Number: 5,757,195
[45] Date of Patent: May 26, 1998

[54] HUMIDITY SENSING CIRCUIT

[75] Inventor: Douglas D. Bird, Dayton, Minn.

[73] Assignee: Honeywell Inc., Minneapolis, Minn.

[21] Appl. No.: 684,354

[22] Filed: Jul. 19, 1996

[51] Int. Cl.⁶ .................................. G01R 27/26
[52] U.S. Cl. ................... 324/678; 324/689; 34/550
[58] Field of Search ........................ 324/678, 677,
324/684, 679; 236/44 C; 338/35; 34/550;
73/780; 361/286; 340/602

[56] References Cited

U.S. PATENT DOCUMENTS 4,563,634  1/1986  Lehle .
4,916,830  4/1990  Braun ........................ 34/550
5,406,137  4/1995  Scheler et al. .

*Primary Examiner*—Christine K. Oda
*Attorney, Agent, or Firm*—Charles L. Rubow

[57] ABSTRACT

A humidity sensing circuit uses a humidity sensitive capacitor as a circuit element in an RC control network for a timer/multivibrator circuit. As the voltage on one plate of the capacitor swings between charge and discharge voltage limits and corresponding triggering voltage values for the timer/multivibrator, the other plate of the capacitor is held at a voltage substantially midway between the charge/discharge voltage limits to thereby cancel out any time averaged net DC component on the capacitor, to reduce stress thereon and extend its life. A power-down feature is disclosed for removing all voltage across the capacitor between sensing intervals.

7 Claims, 2 Drawing Sheets

5,757,195

1

HUMIDITY SENSING CIRCUIT

FIELD OF THE INVENTION

The invention pertains to the field of humidity sensors for use in instrumentation or control systems, and more particularly to an improved circuit for use with a capacitive humidity sensor.

BACKGROUND OF THE INVENTION

Humidity sensors of various types are well known in industry and are utilized in many applications wherein it is necessary to measure or control humidity. A common and very important application is in industrial or residential heating, ventilation and air conditioning (HVAC) systems. In such systems the humidity sensor provides a measure of air humidity in a controlled space or supply system, which is used by the overall HVAC control for managing the air handling equipment to maintain humidity within preselected ranges.

One type of sensor uses a humidity-sensitive film to form a variable capacitor. The film has capacitor electrodes formed on either side thereof, by vacuum deposition of gold or the like. These conductive areas separated by the film form a capacitor, whose capacitance varies as a function of humidity.

A number of different circuits have been developed for utilizing such sensors, and improvements in such circuits have been directed to dealing with problems asociated with the very small amount of capacitance presented by such sensors, and compensating for nonlinearities that may occur in some designs. More recently, efforts have gone into minimizing the amount of DC voltage which is applied across the humidity-sensitive film, or minimizing the amount of time during which said DC voltage is present. This is because of a concern that exposure to DC biases shortens the life and degrades the performance of the sensor element.

SUMMARY OF THE INVENTION

To overcome these and other problems with prior art sensing circuits, the present invention provides an improved humidity sensing circuit for use with a capacitive sensor element. The present invention provides a circuit which is, as compared with prior art designs, simpler, lower in cost, and which effectively eliminates a net DC component from biasing humidity-sensitive the film.

DETAILED DESCRIPTION OF THE PREFERRED EMBODIMENT

Figure 1:
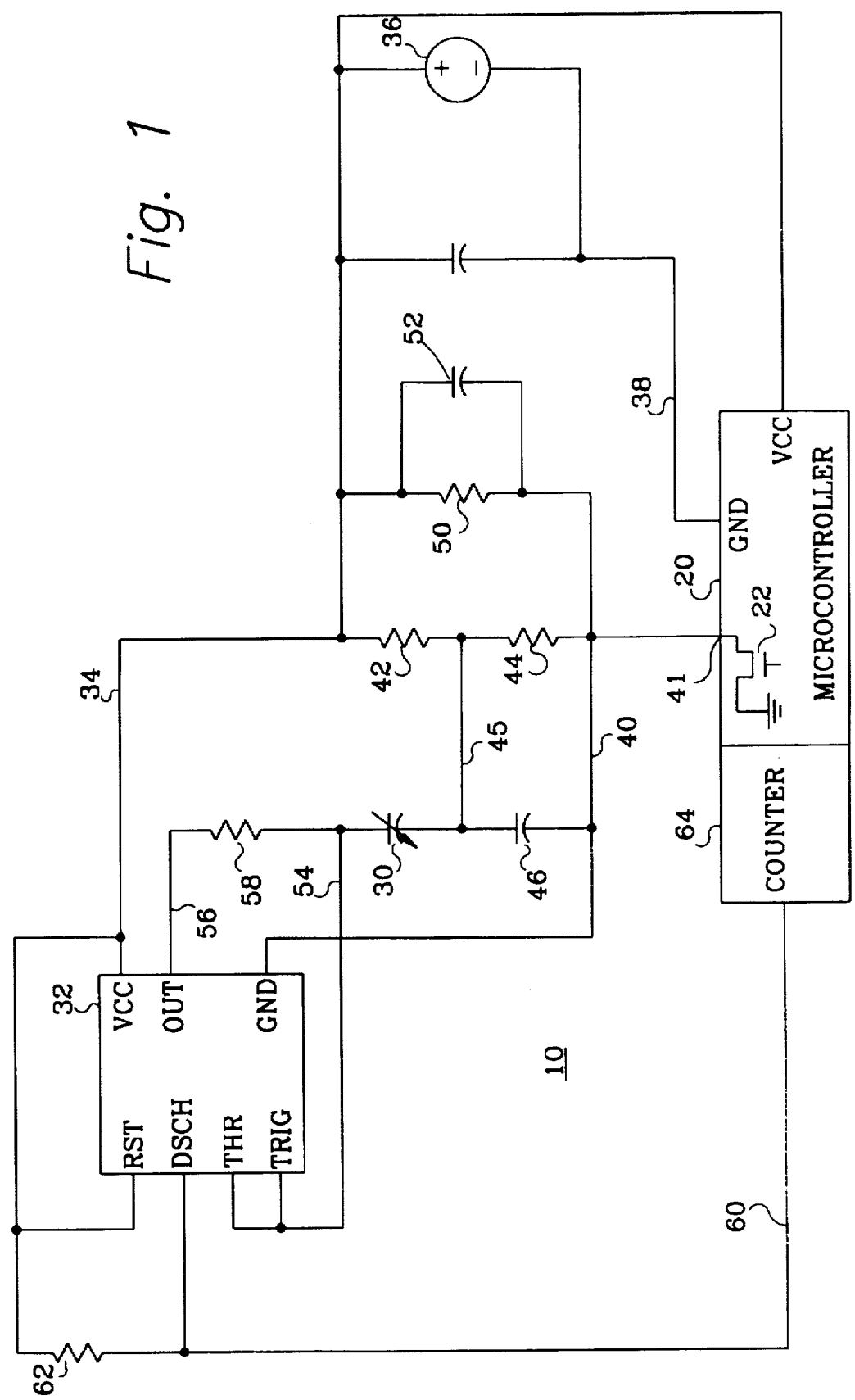
FIG. 1 is a schematic diagram of a circuit according to the present invention.

A presently preferred embodiment of the invention is shown in circuit diagram in FIG. 1. In the preferred embodiment, the sensing circuit is generally indicated by reference number 10. This circuit may be formed on a hybrid circuit module which is mounted on a further circuit board (not shown) for an air temperature/humidity control system. In FIG. 1, a microcontroller 20 is shown as a part of such an overall control system. Since the design, construction and operation of various types of HVAC controls is generally known in the art, and since the improved humidity sensing circuit of the present invention can be used with any type of instrumentation, control or utilization device, the details of such system are not presented here. Only microcontroller 20 is shown, and then only a limited function thereof, as it relates to the integration of the humidity sensing circuit with a HVAC control system.

Humidity sensing circuit 10 generally includes humidity sensing capacitor 30, which may preferably be a known type made from humidity sensitive film. As is generally known such film exhibits characteristics which change in response to humidity, and the film can be coated with conductors such as gold by a vapor deposition process. This process forms electrodes on both sides of the film which act as the plates of a capacitor, with the film as the dielectric. Suitable wire connections are made to the conductive film and brought out for connection to circuit elements. The capacitance of this element is represented in the drawing of FIG. 1 as capacitor 30. In practice, this may amount to something in the range of 150 pf, and the amount of variation therein due to humidity is relatively small. Nonetheless, it can be measured through the circuit of FIG. 1.

Reference number 32 identifier an integrated circuit (IC) of the type commercially available under model designator LMC 555. This is a CMOS version of the familiar 555-type of timer circuit. Operating voltage for the circuit is provided to the VCC terminal of IC 32 via a lead 34, and also to a reset (RST) terminal of the IC. This VCC voltage is fed from a voltage reference source indicated by reference number 36. This may be the power supply for the circuit board or microcontroller or other components of the HVAC control system, or it may be a separate reference, as desired. The plus terminal of voltage reference 36 is connected to a branch of lead 34 to supply VCC to the various components. A branch of this lead is also seen as supplying VCC to microcontroller 20. The negative side of voltage reference source 36 connects through a lead 38 to a ground (GND) terminal of microcontroller 20.

Lead 40 connects to the ground terminal of IC 32, and also to certain other components as described below. However, in the preferred embodiment it does not connect directly to the minus terminal of voltage reference source 36, although it could in other applications. In the preferred embodiment, lead 40 connects through a connector 41 to a terminal of microcontroller 20. As indicated, this terminal connects through an open drain FET switch 22 to an internal ground within microcontroller 20. Switch 22 is simply a representation of an available switch function within the microcontroller. When switch 22 is turned on by action of the microcontroller, it has the effect of connecting lead 40 to the minus reference lead 38 of the voltage reference source 36, via the ground connection within microcontroller 20.

Resistors 42 and 44 connect as a voltage divider between lead 34 (VCC) and lead 40 (the switchable ground). The interconnection point of these resistors connects via lead 45 to one terminal of sensing capacitor 30. A capacitor 46 also connects from lead 45 to lead 40. A resistor 50 and its bypass capacitor 52 also connect between lead 34 and lead 40.

The other terminal of the sensing capacitor 30 connects by way of a lead 54 to both the threshold (THR) and trigger (TRIG) inputs of IC 32. These are used as the first and second triggering voltage levels in the operation of the preferred embodiment, as explained below. The OUT terminal of IC 32 (although it is not used as the output in this particular circuit) connects via lead 56 to one end of a resistor 58, whose other end connects to lead 54 and, therefore, to sensing capacitor 30. The discharge (DSCH) terminal of IC 32, is used as the output of this circuit, and it connects to a lead 60. A pull-up resistor 62 connects from this output to VCC on lead 34. As explained in greater detail below, the output on lead 60 provides the variable frequency switching, the frequency of which is a function of the capacitance of sensing capacitor 30 and, therefore, is a function of the humidity being sensed. Lead 60 is shown going to a counter function 64 within microcontroller 20. The pulses on lead 60 are counted so that the frequency can be used as the measure of humidity, for control or display purposes. It will be appreciated by those skilled in the art of microcontroller system design that lead 60 may in fact go through a multiplexer or other input select devices to an appropriate input of microcontroller 20, and that the counting/frequency detection function can be implemented using software and registers within the microcontroller.

A common general method of operation of a timer such as IC 32 is to use an external RC charging circuit to control the triggering of the timer. Capacitor 30 forms part of an RC charging circuit, so that a voltage waveform is developed across it and applied to the THR and TRIG inputs, causing the OUT and DSCH terminals to be switched between high and low states. This, in turn, controls charging or discharging through the RC circuit. However, this general method of operation would have a disadvantage when applied to this type of circuit. Namely, the operation of the RC charging circuit would leave a net DC voltage component across the capacitor of the RC charging path, which is undesirable for this type of humidity sensing element. The circuit of the present invention solves this problem by providing a special offset or reference for sensing capacitor 30.

IC 32 has internal circuitry which sets the trip point for the THR input at two-thirds VCC and the trip point for the TRIG input at one-third VCC. Thus, in the type of configuration discussed above, the RC circuit consisting of resistor 58 and sensing capacitor 30 charges and discharges such that the voltage at lead 54 increased to two-thirds VCC, the IC changes state, and the voltage at lead 54 then decreases to one-third VCC, after which the IC changes states and the cycle repeats. The DSCH terminal output reflects this switching also and is used as the output signal of the circuit.

Instead of connecting the other side of sensing capacitor 30 (ie. the side not connected to lead 54 and the THR and TRIG inputs) to ground, it is connected to a reference voltage established by a voltage divider to effectively average out any net DC component. Resistors 42 and 44 provide the voltage division for VCC (when lead 40 is connected to ground as described above). In the preferred embodiment, the resistance values of these resistors are chosen to place lead 45 at one-half VCC.

Figure 2:
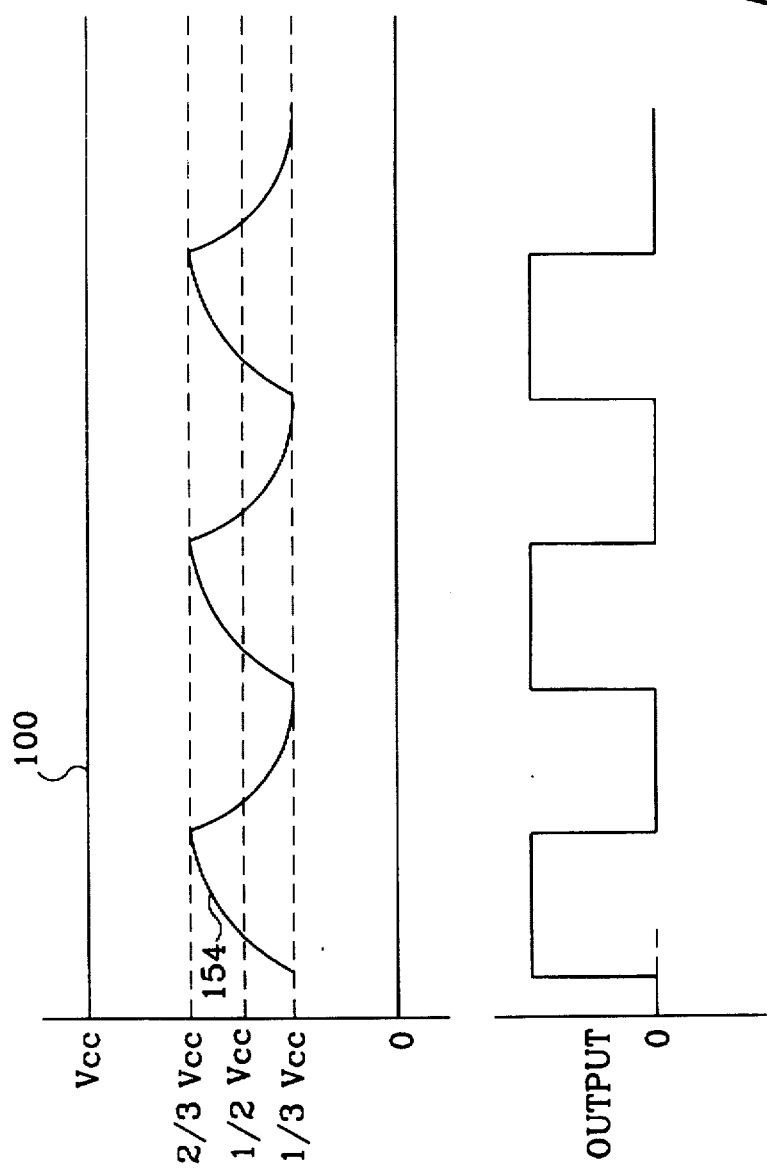
FIG. 2 is graph of waveforms illustrating the operation of the circuit FIG. 1.

Capacitor 46 is much larger than sensing capacitor 30, and is chosen in conjunction with the values of resistors 42 and 44 to essentially stabilize lead 45 at this midpoint voltage. Under these circumstances, as the voltage at lead 54 increases and decreases between one-third VCC and two-thirds VCC, the voltage at any given moment across sensing capacitor 30 is kept at a smaller value, i.e., the difference between one-half VCC and either one-third VCC or two-thirds VCC. This operation is shown in FIG. 2. By suitable choice of the resistance and capacitance values the net DC voltage across sensing capacitor 30 can be essentially averaged out to zero. As pointed out above, this is highly desirable in terms of minimizing degradation and improving the life of sensing capacitor 30. Laser trimming of resistors 42, 44 and/or 58 might also be done for calibration or fine tuning to precise values.

Waveforms illustrating the operation of the circuit are shown in FIG. 2. Line 100 indicates VCC voltage, and the two dotted lines show, respectively, two-thirds and one-third of VCC. The sawtooth line 154 shows the waveform appearing at lead 54 and one side of the sensing capacitor 30. The sawtooth wave results from the charging and discharging of the RC circuit between the two-thirds and one-third VCC switching thresholds. However, it will be appreciated that the other side of sensing capacitor 30, at lead 45, is stabilized at one-half VCC. Therefore, the amount of voltage swing across capacitor 30 is minimized, and also more importantly, the net, time averaged value, is essentially zero.

As a further means of extending the life of sensing capacitor 30, it is desirable to only operate the circuit with a voltage as needed. For many control operations measuring humidity can be done on an intermittent basis, as it is normally not expected to change very quickly. For example, one sample measurement every five minutes or so maybe sufficient.

To accomplish this microcontroller 20 is programmed to provide closure of switch 22 only when a measurement is desired. When switch 22 is closed, lead 40 connects through the GND terminal of microcontroller 20 to the negative terminal voltage reference source 36. In this condition, operating voltage is applied to circuit 10 as previously discussed, and operation commences, producing an output pulse train at lead 60 with a frequency which is a function of the capacitance of sensing capacitor 30. As previously indicated, this may be counted by a counter or a counting function within microcontroller 20, to complete the desired humidity measurement. This may only need about two seconds of operation during that five-minute interval. At the end of a measurement, microcontroller 20 can open switch 22, disconnecting lead 40 from ground and from the negative terminal of the reference voltage source. When this happens the voltage at lead 40 will eventually be brought up to the voltage at lead 34, VCC, as any charges on capacitors in the system bleed off through resistor 50, as well as resistors 42 and 44. Without a ground, both sides of sensing capacitor 30 will be at VCC, and since this is an arbitrary unreferenced voltage at that point, there is no net voltage across the sensing capacitor.

When it is time to make another measurement, microcontroller closes switch 22, which again applies ground to the circuit, and operation as previously described resumes. After a brief settling interval, good data will be reached and another measurement count can be taken.

It will be appreciated from the foregoing that the invention provides an improved humidity sensing circuit which is simple, low in cost, highly accurate, and which avoids placing net DC voltages on the capacitive sensing element, to thereby extend its life.

I claim:

1. A circuit for a variable capacitor humidity sensor, comprising:

a switching circuit having an output and having signal input means for receiving a reference signal, the switching circuit operable for changing between first and second output states in response to the input reference signal moving between predetermined first and second triggering voltage levels;

an RC charging network operatively connected to provide the reference signal to the signal input means such that the charging and discharging of the RC charging network controls periodic switching of the switching circuit between said first and second output states;

the RC charging network including a humidity sensing capacitor whose capacitance varies with humidity such that the frequency of the periodic switching varies with humidity; and a voltage reference circuit connected to apply to the humidity sensing capacitor, a reference voltage having a voltage in relation to the first and second triggering voltage levels to reduce the time-averaged DC voltage across the humidity sensing capacitor during the charging and discharging of the RC charging network, so as to improve the life of the humidity sensing capacitor.

2. A circuit according to claim 1 wherein the value of the reference voltage applied to the humidity sensing capacitor is related to the first and second triggering voltage levels such that the time-averaged DC voltage across the humidity sensing capacitor during the charging and discharging of the RC network is substantially reduced to zero.

3. A circuit according to claim 1 wherein the value of the reference voltage applied to the humidity sensing capacitor is substantially at the mid-point between the first and second triggering voltage levels.

4. A circuit for a variable capacitor humidity sensor, comprising:

a switching circuit having an output and having signal input means for receiving a reference signal, the switching circuit operable for changing between first and second output states in response to the input reference signal moving between predetermined first and second triggering voltage levels;

an RC charging network including a humidity sensing capacitor operatively connected to provide the reference signal from one side of the sensing capacitor to the signal input means, and the RC charging network connected for charging or discharging from an output of the switching circuit such that the charging and discharging of the RC network provides the reference signal to control the periodic switching of the switching circuit between said first and second output states at a frequency which is a function of sensed humidity; and a voltage reference circuit connected to apply a reference voltage to the other side of the humidity sensing capacitor, having a voltage between the first and second triggering voltage levels, to thereby reduce the time-averaged DC voltage across the humidity sensing capacitor during the charging and discharging of said RC charging network to improve life of the capacitor.

5. A circuit according to claim 4 wherein the value of the reference voltage applied to the humidity sensing capacitor is related to the first and second triggering voltage levels such that the time-averaged DC voltage across the humidity sensing capacitor during the charging and discharging of the RC network is substantially reduced to zero.

6. A circuit according to claim 4 wherein the value of the reference voltage applied to the humidity sensing capacitor is substantially at the mid-point between the first and second triggering voltage levels.

7. A circuit according to claim 4 further including standby switching means for selectively removing the reference voltage from said RC charging network to remove voltage from across the humidity sensing capacitor during a standby mode, to further prolong life of the sensor.

* * * * *